United States Patent [19]

Wilcox

[11] 4,046,809
[45] Sept. 6, 1977

[54] N-BENZYL-2,6-DINITRO-3-AMINO-4-TRI-FLUOROMETHYLANILINES AS PLANT GROWTH REGULANTS

[76] Inventor: Merrill Wilcox, 2911 NW. 30th Terrace, Gainesville, Fla. 32601

[21] Appl. No.: 533,045

[22] Filed: Dec. 16, 1974

[51] Int. Cl.$^2$ .............................................. C07C 87/28
[52] U.S. Cl. .................................... 260/570.9; 71/78; 71/121
[58] Field of Search ....................................... 260/570.9

[56] References Cited

U.S. PATENT DOCUMENTS

| 3,227,758 | 1/1966 | Richter et al. | 260/570.9 |
| 3,406,024 | 11/1968 | Richter et al. | 260/570.9 X |
| 3,586,725 | 6/1971 | Hunter | 260/646 |

FOREIGN PATENT DOCUMENTS

| 2,108,346 | 9/1971 | Germany | 260/570.9 |

OTHER PUBLICATIONS

Burger, "Medicinal Chemistry", 2nd Ed., pp. 74-75, (1960).

*Primary Examiner*—Robert V. Hines
*Attorney, Agent, or Firm*—Frederick H. Rabin

[57] ABSTRACT

N-benzyl-2,6-dinitro-3-amino-4-trifluoromethyl-anilines of the formula surface of

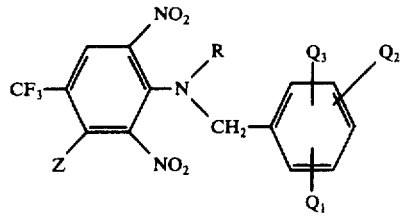

in which
R is lower alkyl,
Z is amino, lower alkylamino or di lower alkylamino,
each of $Q_1$ and $Q_2$ is hydrogen, halogen, lower alkyl or methoxy, and
$Q_3$ is hydrogen, lower alkyl or methoxy, are useful as herbicides and plant growth regulating agents, in particular as agents for controlling the growth of tobacco suckers. Particularly useful are those compounds in which R is ethyl, Z is amino or methylamino, $Q_1$ is methyl, fluorine or chlorine in the ortho-position, $Q_2$ is hydrogen, fluorine or chlorine, and $Q_3$ is hydrogen.

10 Claims, No Drawings

N-BENZYL-2,6-DINITRO-3-AMINO-4-TRIFLUOROMETHYLANILINES AS PLANT GROWTH REGULANTS

DETAILED DISCLOSURE

This invention concerns new N-benzyl-2,6-dinitro-3-amino-4-trifluoromethylaniline compounds, processes for their preparation, methods for regulating plant growth employing these compounds, and compositions containing said compounds as active substances. These compounds are useful for altering the growth pattern of growing plants, and are particularly suited for the retardation and/or control of tobacco suckers, i.e., the undesirable branching of tobacco plants.

More particularly, the invention concerns N-benzyl-2,6-dinitro-3-amino-4-trifluoromethylaniline compounds of the general formula

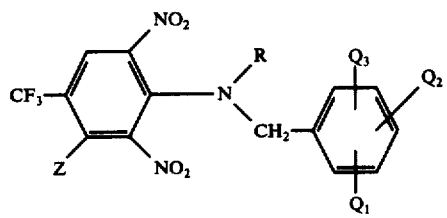

in which

R is a lower alkyl,

Z is amino, lower alkylamino or di lower alkylamino, each of $Q_1$ and $Q_2$ is hydrogen, halogen, lower alkyl or methoxy, and $Q_3$ is hydrogen, lower alkyl or methoxy.

In the foregoing definition, the term "lower alkyl" indicates saturated aliphatic hydrocarbons having no more than 4 carbon atoms. Included within the definition, therefore, are methyl, ethyl, n-propyl, isopropyl, and the four butyl configurations. The term "halogen" refers to fluorine, chlorine, bromine and iodine, in particular to fluorine and chlorine.

Preferred among the compounds of formula (I) are those which have the structure

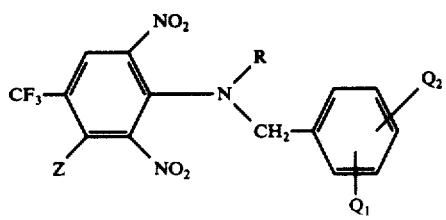

in which

R is methyl or ethyl,

Z is amino, methylamino or ethylamino, and each of $Q_1$ and $Q_2$ is hydrogen, fluorine, chlorine or methyl.

More preferred are compounds of the formula

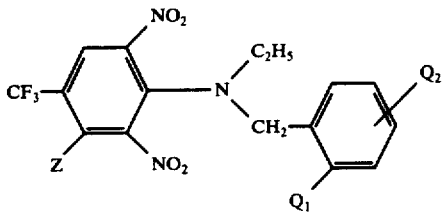

in which

Z is amino or methylamino, $Q_1$ is methyl, fluorine or chlorine, and $Q_2$ hydrogen, fluorine or chlorine.

Particularly preferred are compounds of formula (III) in which Z is amino, $Q_1$ is fluorine or chlorine, and $Q_2$ is in the 6- position.

For plant growth regulating effectiveness, in particular for control of tobacco suckers, the compounds of this invention are preferably applied at a rate of from about 10 to about 400 milligrams per plant. The compounds are most conveniently applied in the form of formulated compositions which will be discussed more fully below. When used at higher concentration, for example, at about 0.5 to about 34 Kg. per hectare, the compounds of this invention act as herbicidal agents. When their use as herbicides is desired, they may be employed as either the sole active ingredient in herbicidal compositions or, alternatively, they may be employed in combination with one of more known herbicidal compounds.

The compounds of formula I may be prepared from a 2,6-dinitro-1,3-dichlorobenzene possessing in its 4- position a trifluoromethyl group (IV).

Substantially equimolar amounts of

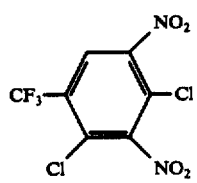

and N-alkylbenzylamine

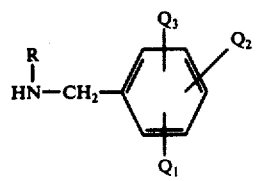

are reacted in the presence of an acid acceptor such as an alkylamine of formula (VI)

The resulting product (VII)

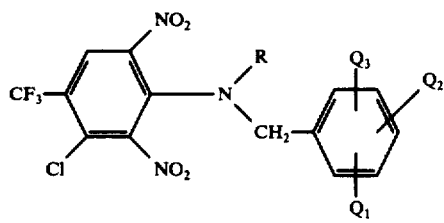

(VII)

need not be isolated but is reacted again with a substantially equimolar amount of

HZ    (VIII)

in the presence of an acid acceptor such as an alkylamine of formula (VI) to yield the compound of formula (I).

In these structures, Z, R, $Q_1$, $Q_2$ and $Q_3$ have the meanings ascribed to them in formula (I).

In both steps, the reactants are dissolved in a suitable aprotic solvent, such as tetrahydrofuran, a dioxane, or a low molecular weight ether. A precipitate of trialkylamine hydrochloride appears and is filtered off at the end of each step. The solvent is evaporated at the end of the second step, and (I) may be recrystallized in a variety of organic solvents or pairs thereof.

The starting materials are readily available or can be prepared by methods well-known in the art. Thus, compounds of formula (IV) may be prepared by nitration of an appropriate chlorobenzene or replacement of the —OH group of a nitrophenol by a chlorine atom. Details concerning the preparation of representative examples of those compounds may be found in Bunnet et al., J.A.C.S. 76, 3936-39 (1954), Friedrich et at. U.S. Pat. No. 2,257,093, Soper U.S. Pat. No. 3,442,639, and Hunter U.S. Pat. No. 3,586,725.

The N-alkylbenzylamines of formula (V) are either commercially available or may be prepared by reductive alkylation of a benzaldehyde and an alkylamine, or conversely, reductive alkylation of a benzylamine and aliphatic aldehyde, as described by Wm. s. Emerson, *Organic Reactions* 4, 174-255 (1948).

The trialkylamine of formula (VI) functions as an acid acceptor. In lieu thereof, other compounds which will form an insoluble salt in the reaction may be used. These compounds include pyridines and alkylpyridines, alkali metal hydroxides, excess substituted benzylamine, or other acid acceptors well known in the art. It is advantageous to use excess benzylamine as the acid acceptor, since the resulting benzylamine hydrochloride may be treated with an inorganic base, thus recovering the substituted benzylamine.

The following examples are intended to illustrate some of the embodiments of this invention. These examples are for illustrative purposes only and are not to be construed as a limitation.

EXAMPLE 1

Equimolar amounts of 2,4-dichloro-3,5-dinitrobenzotrifluoride, N-ethyl-2-chloro-6-fluorobenzylamine, and triethylamine were each dissolved in separate aliquots of tetrahydrofuran. The solutions containing the amines were combined and then added to the benzotrifluoride solution at below 10° C. The final solution was put under a nitrogen atmosphere and allowed to stand for several days. The precipitate of triethylamine hydrochloride (which began forming a few minutes after the final admixture) was then filtered out, leaving a solution of N-(2'-chloro-6'-fluorobenzyl)-N-ethyl-3-chloro-2,6-dinitro-4-trifluoromethylaniline. This solution was used in the next step without isolation or purification. It was brought to −15° C in a reaction bomb, and an excess of liquid ammonia was run into the bomb. The bomb was maintained at −15° C overnight, and vented while cold. Crude N-(2'-chloro-6'-fluorobenzyl)-N-ethyl-3-amino-2,6-dinitro-4-trifluoromethylaniline, melting point 118°-125° C, remained as a cake after evaporation of the solvent. Recrystallization from ether/ ligroine gave a compound with melting point 122°-124° C.

Analysis: $C_{16}H_{13}ClF_4N_4O_4$: Calc: C, 44.00%, N, 12.83%. Found: C, 43.80%, N, 13.15%.

EXAMPLE 2

A crude solution of N-(2'-chloro-6'-fluorobenzyl)-N-n-propyl-3-chloro-2,6-dinitro-4-trifluoromethylaniline in tetrahydrofuran was prepared from N-n-propyl-2-chloro-6-fluorobenzylamine by means of the first reaction described in Example 1. To this crude solution was added a solution of equimolar amounts of triethylamine and anhydrous ethylamine in tetrahyrofuran. The container was put under a nitrogen atmosphere and allowed to stand several days. Evaporation of the solvent left crude N-(2'-chloro-6'-fluorobenzyl)-N-n-propyl-3-ethylamino-2,6-dinitro-6-trifluoromethylaniline, a viscous red oil.

EXAMPLE 3

The method of Example 1 was used to prepare N-(2'-chloro-6'-fluorobenzyl)-N-methyl-3-amino-2,6-dinitro-4-trifluoromethylaniline, melting point 141°-144° C.

Analysis: $C_{15}H_{11}ClF_4N_4O_4$: Calc. C, 42.62%; H, 2.62%; N, 13.25%: Found C, 43.34%, H, 2.82%; N, 13.28%.

EXAMPLE 4

The method of Example 1 was used to prepare N-(2'-chloro-6'-fluorobenzyl)-N-n-propyl-3-amino-2,6-dinitro-4-trifluoromethylaniline, melting point 107°-109° C.

Analysis: $C_{17}H_{14}ClF_4N_3O_4$: Calc. C, 46.86%; H, 3.25%; N, 9.64%. Found: C, 46.83%; H, 3.20%; N, 9.50%.

EXAMPLE 5

The method of Example 1 was used to prepare N-(2'-fluorobenzyl)-N-ethyl-3-amino-2,6-dinitro-4-trifluoromethylaniline, melting point 109°-111° C.

Analysis: $C_{16}H_{14}F_4N_4O_4$: Calc: C, 47.77%; N, 13.93%. Found: C, 47.62%; N, 13.80%.

EXAMPLE 6

The method of Example 1 was used to prepare N-(2'-methylbenzyl)-N-ethyl-3-amino-2,6-dinitro-4-trifluoromethylaniline, melting point 114°-116° C.

Analysis: $C_{17}H_{17}F_3N_4O_4$: Calc: C, 51.26%, N, 14.06%. Found: C, 51.19%; N, 13.96%.

EXAMPLE 7

The method of Example 2 was used to prepare N-(2'-chloro-6'-fluorobenzyl)-N-ethyl-3-methylamino-2,6-dinitro-4-trifluoromethylaniline, melting point 99°-101° C.

Analysis: $C_{17}H_{16}ClF_4N_4O_4$: Calc: C, 45.30%; H, 3.35%, N, 12.43%. Found: C, 45.14%; H, 3.36%; N, 12.55%.

EXAMPLE 8

The method of Example 2 was used to prepare N-(2'-fluorobenzyl)-N-ethyl-3-methylamino-2,6-dinitro-4-trifluoromethylaniline, melting point 110°–112° C.

Analysis: $C_{17}H_{16}F_4N_4O_4$: Calc.: C, 49.04%; N, 13.46%. Found: C, 49.41%; N, 13.35%.

EXAMPLE 9

The method of Example 2 was used to prepare N-(2'-methylbenzyl)-N-ethyl-3-methylamino-2,6-dinitro-4-trifluoromethylaniline, melting point 108°–110° C.

Analysis: $C_{18}H_{19}F_3N_4O_4$: Calc.: C, 52.43% N, 13.59%. Found: C, 52.08%, N, 13.29%.

EXAMPLE 10

The method of Example 2 was used to prepare N-(2'-chlorobenzyl)-N-ethyl-3-methylamino-2,6-dinitro-4-trifluoromethylaniline, melting point 137°–139° C.

Analysis: $C_{17}H_{16}ClF_3N_4O_4$: Calc.: C, 47.18%, N, 12.95%. Found: C, 46.96%; N, 12.96%.

EXAMPLES 11–46

Additional N-benzyl-2,6-dinitro-3-amino-4-trifluoromethylanilines are prepared by methods analogous to Examples 1 and 2, as shown in the following Table.

| Ex. | Z | R | $Q_1$ | $Q_2$ | $Q_3$ | Melting Point °C |
|---|---|---|---|---|---|---|
| 1 | $NH_2$ | $C_2H_5$ | 2-Cl | 6-F | H | 122–124 |
| 2 | $NHC_2H_5$ | $nC_3H_7$ | 2-Cl | 6-F | H | red oil |
| 3 | $NH_2$ | $CH_3$ | 2-Cl | 6-F | H | 141–144 |
| 4 | $NH_2$ | $nC_3H_7$ | 2-Cl | 6-F | H | 107–109 |
| 5 | $NH_2$ | $C_2H_5$ | 2-F | H | H | 109–111 |
| 6 | $NH_2$ | $C_2H_5$ | 2-$CH_3$ | H | H | 114–116 |
| 7 | $NHCH_3$ | $C_2H_5$ | 2-Cl | 6-F | H | 99–101 |
| 8 | $NHCH_3$ | $C_2H_5$ | 2-F | H | H | 110–112 |
| 9 | $NHCH_3$ | $C_2H_5$ | 2-$CH_3$ | H | H | 108–110 |
| 10 | $NHCH_3$ | $C_2H_5$ | 2-Cl | H | H | 137–139 |
| 11 | $NH_2$ | $C_2H_5$ | H | H | H | 130–132 |
| 12 | $NH_2$ | $CH_3$ | H | H | H |  |
| 13 | $NHCH_3$ | $CH_3$ | H | H | H |  |
| 14 | $NHCH_3$ | $CH_3$ | 2-$CH_3O$ | H | H |  |
| 15 | $NH_2$ | $C_2H_5$ | 2-$CH_3O$ | H | H |  |
| 16 | $NH_2$ | $iC_3H_7$ | 2-$CH_3O$ | H | H |  |
| 17 | $NHC_2H_5$ | $CH_3$ | 2-Cl | 6-F | H | 87–88 |
| 18 | $NHCH_3$ | $CH_3$ | 2-Cl | 6-F | H | 85–91 |
| 19 | $NHC_2H_5$ | $C_2H_5$ | 2-Cl | 6-F | H | 82–85 |
| 20 | $NHCH_3$ | $nC_3H_7$ | 2-Cl | 6-F | H | red oil |
| 21 | $NHC_2H_5$ | $iC_3H_7$ | 2-Cl | 6-F | H | red oil |
| 22 | $NH_2$ | $nC_3H_7$ | 2-Cl | 6-F | H |  |
| 23 | $NHC_2H_5$ | $C_2H_5$ | 2-$CH_3$ | H | H | 93–97 |
| 24 | $NHCH_3$ | $C_2H_5$ | 2-$CH_3$ | H | H |  |
| 25 | $NHCH_3$ | $C_2H_5$ | 2-$CH_3$ | 6-$CH_3$ | H |  |
| 26 | $NHCH_3$ | $C_2H_5$ | 2-$CH_3O$ | H | H |  |
| 27 | $NHCH_3$ | $C_2H_5$ | 2-F | 6-F | H |  |
| 28 | $NHCH_3$ | $C_2H_5$ | 2-Cl | 6-Cl | H |  |
| 29 | $NHCH_3$ | $C_2H_5$ | 2-$CH_3$ | 4-$CH_3$ | 6-$CH_3$ |  |
| 30 | $NHCH_3$ | $C_2H_5$ | 2-$CH_3O$ | 4-$CH_3O$ | 6-$CH_3O$ |  |
| 31 | $NH_2$ | $C_2H_5$ | 2-$CH_3O$ | H | H |  |
| 32 | $NH_2$ | $C_2H_5$ | 3-$CH_3$ | H | H |  |
| 33 | $NH_2$ | $C_2H_5$ | 2-Cl | H | H |  |
| 34 | $NH_2$ | $C_2H_5$ | 4-Cl | H | H |  |
| 35 | $NH_2$ | $C_2H_5$ | 2-Cl | 6-Cl | H |  |
| 36 | $NH_2$ | $C_2H_5$ | 2-F | 6-F | H |  |
| 37 | $NH_2$ | $C_2H_5$ | 2-$CH_3O$ | 6-$CH_3O$ | H |  |
| 38 | $NH_2$ | $C_2H_5$ | 2-$CH_3$ | 6-$CH_3$ | H |  |
| 39 | $NH_2$ | $C_2H_5$ | 2-$CH_3O$ | 4-$CH_3O$ | 6-$CH_3O$ |  |
| 40 | $NH_2$ | $C_2H_5$ | 2-$CH_3$ | 4-$CH_3$ | 6-$CH_3$ |  |
| 41 | $NH_2$ | $CH_3$ | 2-F | H | H |  |
| 42 | $NH_2$ | $C_2H_5$ | 3-F | H | H |  |
| 43 | $NH_2$ | $C_2H_5$ | 2-F | 3-F | H |  |
| 44 | $NH_2$ | $C_2H_5$ | 2-F | 5-F | H |  |
| 45 | $NHC_2H_5$ | $C_2H_5$ | 2-F | H | H |  |
| 46 | $NHCH_3$ | $nC_3H_7$ | 2-F | H | H |  |

EXAMPLE 47

Plots of five Hicks tobacco plants on which suckers were beginning to appear were treated with 50 ml. of 50% aqueous acetone containing 0.1% of Triton X-114 sold by Rohm and Hass, an octylphenoxypolyethoxyethanol, and 750 ppm of certain active ingredients. Twenty-five days later, sucker size was rated. Thirty-three days later, the suckers were removed, counted and weighed. The results for various active ingredients are shown in the following table:

| Compound | Sucker Size | No. of suckers on 5 plants | Sucker weight (gm) |
|---|---|---|---|
| N-(2'-methylbenzyl)-N-ethyl-2,6-dinitro-3-amino-4-trifluoromethylaniline (according to this invention) | 1.8 | 7 | 74 |
| N-(2'-chloro-6'-fluorobenzyl)-N-ethyl-2,6-dinitro-3-amino-4-trifluoromethylaniline (according to this invention) | 1.0 | 0 | 0 |
| N-sec.butyl-4-tert.butyl-2,6-dinitroaniline (known compound) | 1.0 | 2 | 14 |
| Maleic hydrazine (known compound) | 2.2 | 17 | 41 |
| Check (untreated) | 4.0 | 14 | 820 |

The rating for sucker size represents the average of 5 plants. A rating of 1 indicates the size of from 0 to 2.5 cm. A rating of 2 indicates the size of from 2.5 to 5.1 cm. A rating of 3 indicates the size of from 5.1 to 10.2 cm. A rating of 4 indicates the size of more than 10.2 cm.

EXAMPLE 48

The procedure of Example 47 was repeated using other plots of five Hicks tobacco plants. After 33 days, suckers were removed, counted and weighed. The results for various active ingredients are shown in the following table:

| Compound | No. of Suckers on 5 plants | Sucker weight (gms) |
|---|---|---|
| N-(2'-fluorobenzyl)-N-ethyl-3-methylamino-2,6-dinitro-4-trifluoromethylaniline (according to this invention) | 0 | 0 |
| N-(2'-chloro-6'-fluorobenzyl)-N-ethyl-3-amino-2,6-dinitro-4-trifluoromethylaniline (according to this invention | 0 | 0 |
| N-sec.butyl-4-tert.butyl-2,6-dinitroaniline (known compound) | 1 | 15 |
| check (untreated) | 17 | 940 |

EXAMPLE 49

Herbicidal compositions comprising various N-benzyl-2,6-dinitro-3-amino-4-trifluoromethylanilines were prepared by finely grinding the active ingredient with potassium chloride, suspending a 0.1% aqueous nonylphenoxy poly(ethyleneoxy)ethanol non-ionic surfactant (Igepal CO-890, sold by GAF Corporation). Seeds were pushed into the soil surface and the herbicidal compositions were applied at a rate of 2.2 Kg. of active ingredient per hectare. Ten days after treatment, the stand and vigor as a percentage of the untreated control were recorded and tabulated. At the same time, parallel tests under the same conditions and with the same active ingredient concentrations were run for trifluralin (N,N-di-n-propyl-2,6-dinitro-4-trifluoromethylaniline). The data obtained are reported below in the following table.

| Compound of Example No. | | Ryegrass Lolium multiform | Coker 67 Corn Zea mays | Giant Grey Stripe Sunflower Helianthus annuus | Rutgers Tomato Lycopersicon esculentum | Florida Broad Leaf Mustard Brassica juncea |
|---|---|---|---|---|---|---|
| 1 | stand % | 0 | 100 | 100 | 90 | 100 |
|  | vigor % | 0 | 30 | 100 | 20 | 60 |
| 3 | stand % | 0 | 100 | 100 | 100 | 100 |
|  | vigor % | 0 | 60 | 100 | 40 | 70 |
| 6 | stand % | 0 | 100 | 100 | 100 | 100 |
|  | vigor % | 0 | 30 | 100 | 50 | 50 |
| 8 | stand % | 0 | 100 | 100 | 80 | 100 |
|  | vigor % | 0 | 50 | 100 | 20 | 60 |
| Trifluralin | stand % | 0 | 100 | 100 | 100 | 100 |
|  | vigor % | 0 | 30 | 70 | 50 | 50 |
| Carrier Control Check | stand % | 100 | 100 | 100 | 100 | 100 |
|  | vigor % | 100 | 100 | 100 | 100 | 100 |
|  | stand % | 100 | 100 | 100 | 100 | 100 |

The production of herbicidal compositions according to the invention is carried out in a manner well-known in the art by the intimate mixing and grinding of the active substances of the general formula I with suitable carriers, optionally with the addition of dispersing agents or solvents which are inert to the active substances. The active substances can exist and be used in the following forms:

as solids: dusts, sprinkling agents, granulates, coated granules, impregnated granules and homogeneous granules;
as concentrates of active substances dispersible in water: wettable powder, pastes, emulsions;
as liquids: solutions, aerosols.

To produce the solid forms (dusts, sprinkling agents, granulates), the active substances are mixed with solid carriers. Suitable carriers are, e.g., kaolin, talcum, bole, chalk, limestone, ground limestone, dolomite, diatomaceous earth precipitated silicic acid, alkaline earth silicates, sodium and potassium aluminum silicates (feldspar and mica), calcium and magnesium sulfates, magnesium oxide, ground synthetic plastics, fertilizers such as ammonium sulfate, ammonium phosphate, ammonium nitrate, ureas, ground vegetable products such as grain flour, bark flour, sawdust, ground nut shells, cellulose powder, residues of plant extractions, activated charcoal, etc. These carriers can be used separately or they can be mixed with each other.

The grain size of the carriers is, for dusts, advantageously up to ca. 0.1 mm, for sprinkling agents it is ca. 0.075 to 0.2 mm and for granulates 0.2 mm upwards.

The concentrations of active substances in the solid preparations are, as a rule, 0.5 to 80% of the total weight.

To these mixtures can also be added additives which stabilize the active substance and/or non-ionic, anion-active and cation-active substances, which, for example, improve the adhesion of the active substances on plants and parts of plants (glues and adhesives) and/or ensure a better wettability (wetting agents) and also dispersibility (dispersing agents). The following are examples of adhesives: olein-chalk mixtures, cellulose derivatives (methyl cellulose, carboxymethyl cellulose), hydroxyethyl glycol·ethers of mono- and di-alkyl phenols having 5 to 15 ethylene oxide radicals per molecule and 8 or 9 carbon atoms in the alkyl radical, lignin sulfonic acids, their alkali and alkaline earth metal salts, polyethylene glycol ethers, fatty alcohol polyethylene glycol ethers having 5 to 20 ethylene oxide radicals per molecule and 8 to 18 carbon atoms in the fatty alcohol part, condensation products of ethylene oxide, propylene oxide, polyvinyl pyrrolidones, polyvinyl alcohols, condensation products of urea/formaldehyde as well as Latex products.

Concentrates of active substances which can be dispersed in water (wettable powders), pastes and emulsion concentrates, are agents which can be diluted with water to give any desired concentration. The consist of active substances, carriers, optionally additives which stabilize the active substance, surface agent substances and antifoaming agents and, optionally, solvents. The concentration of active substance in these agents is 5 to 80% of the total weight of the latter.

The wettable powders and pastes are obtained by mixing and grinding the active substances with dispersing agents and pulverulent carriers in suitable devices until homogeneity is attained. Suitable carriers are, for example, those previously mentioned for solid preparations. It is advantageous in some cases to use mixtures of different carriers. Suitable dispersing agents are, e.g., condensation products of sulfonated naphthalene and sulfonated naphthalene derivatives with formaldehyde, condensation products of naphthalene or of naphthalene sulfonic acids with phenol- and formaldehyde, also alkali, ammonium and alkaline earth metal salts of lignin sulfonic acid, also alkylaryl-sulfonates, alkali and alkaline earth metal salts of dibutyl naphthalene sulfonic acid, fatty alcohol sulfates such as salts of sulfated fatty alcohol glycol ethers, the sodium salt of oleyl ethinate, the sodium salt of oleyl methyl tauride, ditertiary acetylene glycols, dialkyldilauryl ammonium chloride and fatty acid alkali and alkaline earth metal salts.

Examples of anti foaming agents are silicones, etc. The active substances are so mixed, ground, sieved and strained with the above-mentioned additives that the solid particle size in wettable powders does not exceed 0.02–0.04 mm and, in the case of pastes, 0.003 mm. To produce emulsion concentrates and pastes, dispersing agents such as those stated in the previous sections, organic solvents and water are used. Examples of solvents are: alcohols, benzene, xylenes, toluene, dimethyl sulfoxide and mineral oil fractions boiling between 120° and 350° C. The solvents must be practically without smell, not phytotoxic, inert to the active substances and not easily flammable.

In addition, the agents according to the invention can be used in the form of solutions. For this application, the active substances or substances of the general formula I are dissolved in suitable organic solvents, mixtures of solvents or in water. Aliphatic and aromatic hydrocarbons, chlorinated derivatives thereof, alkyl naphthalenes, mineral oils, on their own or mixed with each other, can be used as organic solvents. The solvents should contain the active substances within a concentration range of 1 to 20% calculated on the total weight of the resulting solution.

Other biocidal active substances or agents can be mixed with the described compositions according to the invention. Thus, in addition to the stated compounds of the general formula I and other herbicides, the new agents can also contain, e.g., insecticides, fungicides, bactericides, fungistatics, bacteriostatics or nematocides in order to widen the range of action. The compositions according to the invention can also contain fertilizers and micronutrients.

I claim:

1. A compound of the formula

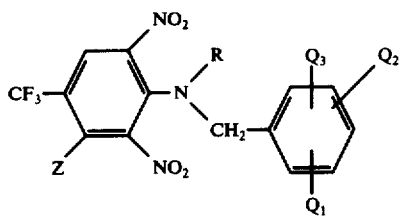

in which

R is lower alkyl,

Z is amino, lower alkylamino or di lower alkylamino, each of $Q_1$ and $Q_2$ is hydrogen, halogen, lower alkyl or methoxy, and $Q_3$ is hydrogen, lower alkyl or methoxy.

2. A compound according to claim 1 in which Z is amino, methylamino or ethylamino; R is methyl or ethyl; each of $Q_1$ and $Q_2$ is hydrogen, fluorine, chlorine or methyl; and $Q_3$ is hydrogen.

3. A compound according to claim 1 of the formula

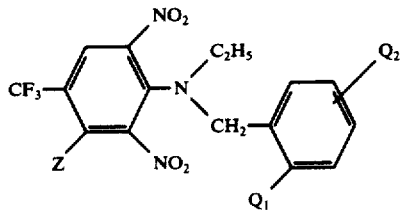

in which

Z is amino or methylamino, $Q_1$ is methyl, fluorine or chlorine, and $Q_2$ is hydrogen, fluorine or chlorine.

4. A compound according to claim 3 in which Z is amino, $Q_1$ is fluorine or chlorine, and $Q_2$ is in the 6-position.

5. The compound of claim 4 which is N-(2'-chloro6'-fluorobenzyl)-N-ethyl-3-amino-2,6-dinitro-4-trifluoromethylaniline.

6. The compound of claim 2 which is N-(2'-chloro-6'-fluorobenzyl)-N-methyl-3-amino-2,6-dinitro-4-trifluoromethylaniline.

7. The compound of claim 3 which is N-(2'-methylbenzyl)-N-ethyl-3-amino-2,6-dinitro-4-trifluoromethylaniline.

8. The compound of claim 3 which is N-(2'-fluorobenzyl)-N-ethyl-3-methylamino-2,6-dinitro-4-trifluoromethylaniline.

9. The compound of claim 3 which is N-(2'-chlorobenzyl)-N-ethyl-3-methylamino-2,6-dinitro-4-trifluoromethyaniline.

10. The compound of claim 1 which is N-(2'-methoxybenzyl)-N-ethyl-3-amino-2,6-dinitro-4-trifluoromethylaniline.

* * * * *